US005578479A

United States Patent [19]

Laderman et al.

[11] Patent Number: 5,578,479

[45] Date of Patent: Nov. 26, 1996

[54] ALPHA-AMYLASE FROM HYPERTHERMOPHILIC ARCHAEBACTERIUM

[75] Inventors: Kenneth Laderman; Christian B. Anfinsen, both of Baltimore, Md.

[73] Assignee: The Johns Hopkins University, Baltimore, Md.

[21] Appl. No.: 893,928

[22] Filed: Jun. 9, 1992

[51] Int. Cl.[6] .............................. C12N 9/28; C12N 1/20; C12P 19/14

[52] U.S. Cl. ......................... 435/202; 435/99; 435/252.1; 435/822

[58] Field of Search .................................... 435/202, 220, 435/99, 252.1, 822; 530/416

[56] References Cited

U.S. PATENT DOCUMENTS

| | | | |
|---|---|---|---|
| 3,969,538 | 7/1976 | Schwengers et al. | 435/201 X |
| 4,600,693 | 7/1986 | Kindle et al. | 435/202 X |
| 4,778,760 | 10/1988 | Ishida et al. | 435/202 |
| 4,929,557 | 5/1990 | Antranikian et al. | 435/202 |
| 5,188,956 | 2/1993 | Nanmori et al. | 435/202 X |
| 5,366,883 | 11/1994 | Asada et al. | 435/202 |
| 5,370,997 | 12/1994 | Antranikian et al. | 435/202 X |

FOREIGN PATENT DOCUMENTS

| | | |
|---|---|---|
| 0157638 | 10/1985 | European Pat. Off. . |
| 9011352 | 10/1990 | WIPO . |

OTHER PUBLICATIONS

Deutscher, Murray P., "Guide to Protein Purification," *Methods in Enzymology,* v. 182, pp. 309–317, 488–495.

Koch, R. et al, "Extremely thermostable amylolytic enzyme from the archaebacterium *Pyrocessus furiosers,*" FEM Microbiology Letters (71) 1990, pp. 21–26.

Sakano et al, "Enzymatic Properties and Action Patterns of Thermactinomyces vulgaris α–Amylase", Agricultural and Biological Chemistry, vol. 46, No. 5, 1982, pp. 1121–1129.

Fukusumi et al, "Cloning and nucleotide sequence of a heat–stable amylase gene from an anaerobic thermophile, Dictyoglomus thermophilum", European Journal of Biochemistry, vol. 174, No. 1, 1988 pp. 15–21.

Linke et al, "Production of heat–stable pullulanase and alpha–glucosidase from the extreme thermophilic archaeon *Pyrococcus woesei*—thermostable enzyme purification and characterization," Dechema Biotechnology Conferences, vol. 5, No. A, 3 Jun. 1992, pp. 161–163.

Kelly et al, "Physiological and biochemical characteristics of hydrolytic enzymes from *Pyrococcus furiosus,*" Life Sciences Collection, Cambridge, MD Ab. No. 82002582692.

Koch, "Purification and properties of a hyperthermoactive α–amylase from the archaebacterium *Pyrococcus woesei*", Arch. Microbiol. (1991) 155:572–578.

Brown et al, "Characterization of Amylolytic Enzyme Activites Associated with the Hyperthermophilic Archaebacterium *Pyrococcus furiosus*", Applied and Environmental Microbiology, Jul. 1990, pp. 1985–1991.

*Primary Examiner*—Robert J. Warden
*Assistant Examiner*—E. Leigh Dawson
*Attorney, Agent, or Firm*—Cushman Darby & Cushman, L.L.P.

[57] ABSTRACT

The present invention relates, in general, to α-amylase, and, in particular to α-amylase from a hyperthermophilic archaebacterium, wherein said α-amylase is in pure form. The invention also relates to a method of purifying a hyperthermophilic α-amylase.

7 Claims, 13 Drawing Sheets

95 °C
60 °C
20 °C
FLUORESCENCE INTENSITY
0
1000
2000
3000
4000
5000
WAVELENGTH (nm)
300
350
400
450
500

5000
4000
3000
2000
1000
0
FLUORESCENCE INTENSITY
20.1
40.1
60.1
80.1
TEMPERATURE (°C)

FIG. 9A

```
                                                                             met
gly asp lys ile asn phe ile phe gly ile his asn his gln pro leu gly asn phe gly
trp val phe glu glu ala tyr glu lys cys tyr trp pro phe leu glu thr leu glu glu
tyr pro asn met lys val ala ile his thr ser gly pro leu ile glu trp leu gln asp
ile arg pro glu tyr ile asp leu leu arg ser leu val lys arg gly gln val glu ile
val val ala gly phe tyr glu pro val leu ala ser ile pro lys glu asp arg ile glu
gln ile arg leu met lys glu trp ala lys ser ile gly phe asp ala arg gly val trp
leu thr glu arg val trp gln pro glu leu val lys thr leu lys glu ser gly ile asp
tyr val ile val asp asp tyr his phe met ser ala glu leu ser lys glu glu leu tyr
trp pro tyr tyr thr glu asp gly gly glu val ile ala val phe pro ile asp glu lys
```

FIG. 9B leu arg tyr leu ile pro phe arg pro val asp lys val leu glu tyr leu his ser leu
ile asp gly asp glu ser lys val ala val phe his asp asp gly glu lys phe gly ile
trp pro gly thr tyr glu trp val tyr glu lys gly trp leu arg glu phe phe asp arg
ile ser ser asp glu lys ile asn leu met leu tyr thr glu tyr leu glu lys tyr lys
pro arg gly leu val tyr leu pro ile ala ser tyr phe glu met ser glu trp ser leu
pro ala lys gln ala arg leu phe val glu phe val asn glu leu lys val lys gly ile
phe glu lys tyr arg val phe val arg gly gly ile trp lys asn phe phe tyr lys tyr
pro glu ser asn tyr met his lys arg met leu met val ser lys leu val arg asn asn
pro glu ala arg lys tyr leu leu arg ala gln cys asn asp ala tyr trp his gly leu
phe gly gly val tyr leu pro his leu arg arg ala ile trp asn asn leu ile lys ala
asn ser tyr val ser leu gly lys val ile arg asp ile asp tyr asp gly phe glu glu
val leu ile glu asn asp asn phe tyr ala val phe lys pro ser tyr gly gly ser leu
val glu phe ser ser lys asn arg leu val asn tyr val asp val leu ala arg arg trp
glu his tyr his gly tyr val glu ser gln phe asp gly val ala ser ile his glu leu
glu lys lys ile pro asp glu ile arg lys glu val ala tyr asp lys tyr arg arg ser
met leu gln asp his val val pro leu gly thr thr leu glu asp phe met phe ser arg
gln gln glu ile gly glu phe pro arg val pro tyr ser tyr glu leu leu asp gly gly
ile arg leu lys arg glu his leu gly ile glu val glu lys thr val lys leu val asn
asp gly phe glu val glu tyr ile val asn asn lys thr gly asn pro val leu phe ala
val glu leu asn val ala val gln ser ile met glu ser pro gly val leu arg gly lys
glu ile val val asp asp lys tyr ala val gly lys phe ala leu lys phe glu asp glu
met glu val trp lys tyr pro val lys thr leu ser gln ser glu ser gly trp asp leu
ile gln gln gly val ser tyr ile val pro ile arg leu glu asp lys ile arg phe lys
leu lys phe glu glu ala ser gly AMB

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 650 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Met Gly Asp Lys Ile Asn Phe Ile Phe Gly Ile His Asn His Gln Pro
1               5                   10                  15

Leu Gly Asn Phe Gly Trp Val Phe Glu Glu Ala Tyr Glu Lys Cys Tyr
            20                  25                  30

Trp Pro Phe Leu Glu Thr Leu Glu Glu Tyr Pro Asn Met Lys Val Ala
        35                  40                  45

Ile His Thr Ser Gly Pro Leu Ile Glu Trp Leu Gln Asp Asn Arg Pro
    50                  55                  60

Glu Tyr Ile Asp Leu Leu Arg Ser Leu Val Lys Arg Gly Gln Val Glu
65                  70                  75                  80

Ile Val Val Ala Gly Phe Tyr Glu Pro Val Leu Ala Ser Ile Pro Lys
                85                  90                  95

Glu Asp Arg Ile Glu Gln Ile Arg Leu Met Lys Glu Trp Ala Lys Ser
            100                 105                 110

Ile Gly Phe Asp Ala Arg Gly Val Trp Leu Thr Glu Arg Val Trp Gln
        115                 120                 125

Pro Glu Leu Val Lys Thr Leu Lys Glu Ser Gly Ile Asp Tyr Val Ile
    130                 135                 140

Val Asp Asp Tyr His Phe Met Ser Ala Gly Leu Ser Lys Glu Glu Leu
145                 150                 155                 160

Tyr Trp Pro Tyr Tyr Thr Glu Asp Gly Gly Glu Val Ile Ala Val Phe
                165                 170                 175

Pro Ile Asp Glu Lys Leu Arg Tyr Leu Ile Pro Phe Arg Pro Val Asp
            180                 185                 190

Lys Val Leu Glu Tyr Leu His Ser Leu Ile Asp Gly Asp Glu Ser Lys
        195                 200                 205

Val Ala Val Phe His Asp Asp Gly Glu Lys Phe Gly Ile Trp Pro Gly
    210                 215                 220

Thr Tyr Glu Trp Val Tyr Glu Lys Gly Trp Leu Arg Glu Phe Phe Asp
225                 230                 235                 240

Arg Ile Ser Ser Asp Glu Lys Ile Asn Leu Met Leu Tyr Thr Glu Tyr
                245                 250                 255

Leu Glu Lys Tyr Lys Pro Arg Gly Leu Val Tyr Leu Pro Ile Ala Ser
            260                 265                 270

Tyr Phe Glu Met Ser Glu Trp Ser Leu Pro Ala Lys Gln Ala Arg Leu
        275                 280                 285

Phe Val Glu Phe Val Asn Glu Leu Lys Val Lys Gly Ile Phe Glu Lys
    290                 295                 300

Tyr Arg Val Phe Val Arg Gly Gly Ile Trp Lys Asn Phe Phe Tyr Lys
305                 310                 315                 320
```

-continued

Tyr Pro Glu Ser Asn Tyr Met His Lys Arg Met Leu Met Val Ser Lys
325 330 335

Leu Val Arg Asn Asn Pro Glu Ala Arg Lys Tyr Leu Leu Arg Ala Gln
340 345 350

Cys Asn Asp Ala Tyr Trp His Gly Leu Phe Gly Gly Val Tyr Leu Pro
355 360 365

His Leu Arg Arg Ala Ile Trp Asn Asn Leu Ile Lys Ala Asn Ser Tyr
370 375 380

Val Ser Leu Gly Lys Val Ile Arg Asp Ile Asp Tyr Asp Gly Phe Glu
385 390 395 400

Glu Val Leu Ile Glu Asn Asp Asn Phe Tyr Ala Val Phe Lys Pro Ser
405 410 415

Tyr Gly Gly Ser Leu Val Glu Phe Ser Ser Lys Asn Arg Leu Val Asn
420 425 430

Tyr Val Asp Val Leu Ala Arg Arg Trp Glu His Tyr His Gly Tyr Val
435 440 445

Glu Ser Gln Phe Asp Gly Val Ala Ser Ile His Glu Leu Glu Lys Lys
450 455 460

Ile Pro Asp Glu Ile Arg Lys Glu Val Ala Tyr Asp Lys Tyr Arg Arg
465 470 475 480

Phe Met Leu Gln Asp His Val Val Pro Leu Gly Thr Thr Leu Glu Asp
485 490 495

Phe Met Phe Ser Arg Gln Gln Glu Ile Gly Glu Phe Pro Arg Val Pro
500 505 510

Tyr Ser Tyr Glu Leu Leu Asp Gly Gly Ile Arg Leu Lys Arg Glu His
515 520 525

Leu Gly Ile Glu Val Glu Lys Thr Val Lys Leu Val Asn Asp Gly Phe
530 535 540

Glu Val Glu Tyr Ile Val Asn Asn Lys Thr Gly Asn Pro Val Leu Phe
545 550 555 560

Ala Val Glu Leu Asn Val Ala Val Gln Ser Ile Met Glu Ser Pro Gly
565 570 575

Val Leu Arg Gly Lys Glu Ile Val Val Asp Asp Lys Tyr Ala Val Gly
580 585 590

Lys Phe Ala Leu Lys Phe Glu Asp Glu Met Glu Val Trp Lys Tyr Pro
595 600 605

Val Lys Thr Leu Ser Gln Ser Glu Ser Gly Trp Asp Leu Ile Gln Gln
610 615 620

Gly Val Ser Tyr Ile Val Pro Ile Arg Leu Glu Asp Lys Ile Arg Phe
625 630 635 640

Lys Leu Lys Phe Glu Glu Ala Ser Gly Xaa
645 650

( 2 ) INFORMATION FOR SEQ ID NO:2:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Thr Leu Asn Asp Met Arg Gln Glu Tyr Tyr Phe Lys
1 5 10

-continued ( 2 ) INFORMATION FOR SEQ ID NO:3:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

```
Xaa Asp Lys Ile Asn Phe Ile Phe Gly Ile His Asn His Gln Pro Leu
1               5                   10                  15

Gly Asn
```

ALPHA-AMYLASE FROM HYPERTHERMOPHILIC ARCHAEBACTERIUM

TECHNICAL FIELD

The present invention relates, in general, to α-amylase, and, in particular to α-amylase from a hyperthermophilic archaebacterium, wherein said α-amylase is in pure form. The invention also relates to a method of purifying a hyperthermophilic α-amylase.

BACKGROUND OF THE INVENTION

The discovery of hyperthermophilic archaebacteria has provided a valuable commercial and research tool. The intrinsic thermal stability of the enzymes isolated from these sources is maintained without any components unique to thermophiles, suggesting that the increase in molecular stability is accomplished through the same stereochemical interactions found in their mesophilic counterparts. The characteristic range of activity observed in hyperthermophilic enzymes tends to parallel growth temperature, there being little or no activity at temperatures which would be optimal for their mesophilic counterparts.

Alpha-amylases are of industrial importance and thus this enzyme is a popular subject for study. Alpha-amylases have been purified from a variety of species spanning the range of thermostability from mesophiles (Takagi et al, Bacterial and Mold Amylases The Enzymes, New York, Academic Press (1971), moderate thermophiles (Antranikian, Applied Biochemistry and Biotechnology 20/21:267–279 (1989); Glymph et al, Applied and Environmental Microbiology 34(4):391 (1977)); Hasegawa et al, J. Biochem. 79:35–42 (1976)) to hyperthermophiles (Koch et al, Arch. Microbiol. 155:572–578 (1991); Schumann et al, FEBS Letters. 282(1): 122–126 (1991)).

*Pyrococcus furiosus* is an anaerobic marine heterotroph with an optimal growth temperature of 100° C., isolated by Fiala and Stetter from solfataric mud off the coast of Vulcano Island, Italy (Fiala et al, Arch. Microbiol. 145:56–61 (1986)). Alpha-amylase activity has been reported in the cell homogenate and growth medium of *P. furiosus* (Brown et al, Applied and Environmental Microbiology. 56(7):1985–1991 (1990); Koch et al, FEMS Microbiology Letters. 71:21–26 (1990)) but purification of this enzyme has not been reported.

The present invention provides α-amylase from *P. furiosus* in purified form and a method of effecting that purification.

SUMMARY OF THE INVENTION

It is a general object of the invention to provide a hyperthermophilic α-amylase in pure form.

Specifically, the invention provides a pure form of *P. furiosus* α-amylase, and compositions comprising same. The invention also provides a method of purifying hyperthermophilic α-amylase.

Further objects and advantages of the invention will be clear from the description that follows.

BRIEF DESCRIPTION OF THE DRAWINGS

FIG. 9A and 9B: Amino acid sequence of α-amylase from *P. furiosus* is given by these figures taken together. This is also shown as as SEQ ID NO:1.

DETAILED DESCRIPTION OF THE INVENTION

Figure 1A:
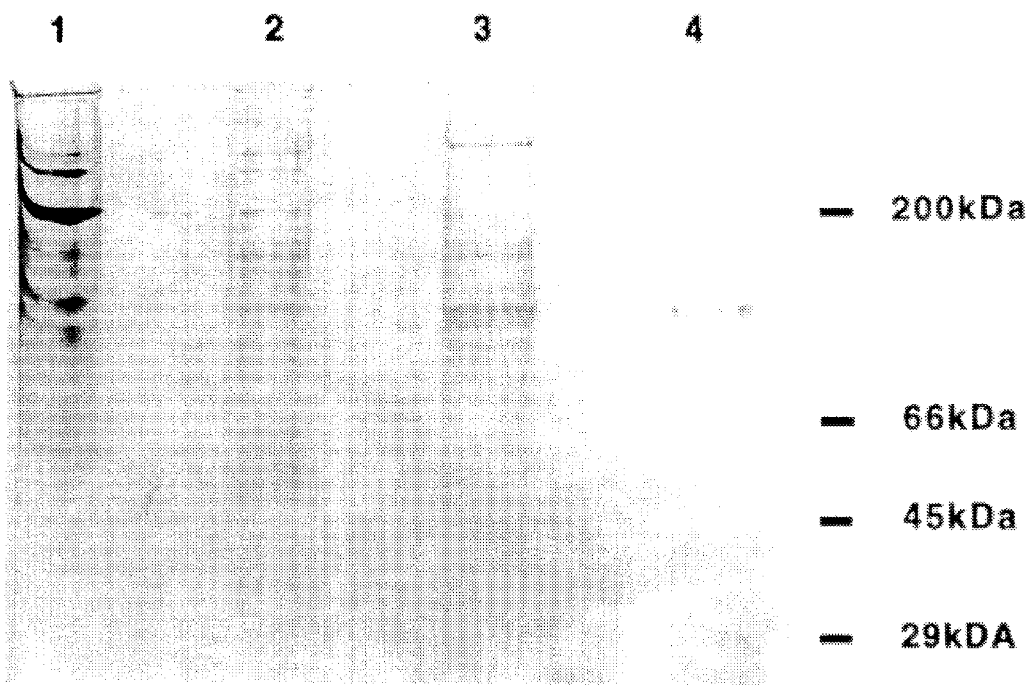
FIG. 1: Electrophoretic characterization of *P. furiosus* amylase purification. (A) Native polyacrylamide gel electrophoresis (8% acrylamide). Lanes: 1, active fraction following ion exchange #1; 2, 3, and 4, active fractions following ion exchange #2, ion exchange #3 and electroelution respectively. (B) Isoelectric focusing of purified amylase on a Phast-System IEF gel with a pH 3–9 gradient (Pharmacia).

The present invention relates to a method of purifying hyperthermophilic α-amylase from archaebacteria and to a pure form of such an α-amylase, specifically, *P. furiosus* α-amylase.

The α-amylase of the invention is distinct from hyperthermophilic α-amylases previously reported in that no significant binding to substrate occurs at temperatures below that required for enzyme activity (while the α-amylase of the invention displays optimal activity at about 100° C., an onset of activity is observed at about 40° C., with a substantial loss of activity being observed at 120° C). The α-amylase of the invention is also distinct in that it displays a capacity for recognition of substrate with a low degree of polymerization. Substrate specificity determinations indicate that glucose polymers as short as maltotriose can serve as substrate.

In a preferred embodiment, the α-amylase of the invention is *P. furiosus* α-amylase having the amino acid sequence given in FIG. 9. The invention also relates, however, to portions of the sequence given in FIG. 9 of at least 12 contiguous amino acids (for example, T-L-N-D-M-R-Q-E-Y-Y-F-K (SEQ ID NO:2) or G/M-D-K-I-N-F-I-F-G-I-H-N-H-Q-P-L-G-N (SEQ ID NO:3)), preferably at least 25 contiguous amino acids, more preferably at least 35 contiguous amino acids and most preferably at least 75 contiguous amino acids. The invention relates also to a single subunit of *P. furiosus* α-amylase.

The α-amylase of the invention can be present in substantially pure form, that is, in a form substantially free of proteins and nucleic acids with which it is normally associated. In a preferred embodiment, the purity of the α-amylase is such that a single band is seen on isoelectric focussing, and a single molecular weight is determinable by analytical ultracentrifugation.

The method used to purify the α-amylase of the invention comprises, as a first step, the preparation of a crude hyperthermophilic archaebacteria cell extract. The cytosolic fraction of that extract is then subjected to ion exchange chromatography, followed by electroelution. The ion exchange chromatography can be carried out using an anion exchange resin that is stable across the pH range of 5–11. The method the present invention results in an α-amylase of sequenceable purity.

The purified α-amylase of the invention has several industrial applications. Glucopolymers with varying degrees of polymerization are utilized in papermaking, textile preparation, brewing and fermentation. The use of purified enzyme in these settings would make it possible to use small quantities of the proteinaceous preparation. Reducing the overall amount of protein required to be added is a significant advantage from the standpoint of safety.

The hydrolysis of α-1,4 glucosidic bonds in an endo-fashion is known industrially as liquefaction. Due to the high viscosities and mass transfer problems, industrial liquefaction is carried out at the highest possible temperature. The thermostability of the α-amylase of the present invention renders this enzyme ideally suited for use in industrial liquefaction in that the thermostability of the enzyme results in more efficient hydrolysis at extreme temperature.

The purified α-amylase of the invention can be formulated dependent upon the application or it can be prepared in bulk form as a purified powder. Bulking agents (such as sucrose, mannitol or arginine) can be included with the powder. Alternatively, α-amylase can be formulated with a neutral buffer of ionic strength, for example 50 mM.

The following non-limiting Examples describe certain aspects of the invention in greater detail. While the following Examples do not include the preparation of antibodies, polyclonal or monoclonal, to the α-amylase of the invention, one skilled in the art will appreciate that such antibodies, or binding fragments thereof, can be prepared using methods known in the art.

EXAMPLES

The following experimental details are referenced in the specific Examples that follow:

Bacterial Strains and Culture Conditions

All of the cultures of *Pyrococcus furiosus* used in the studies described herein employed strain DSM 3638, originally obtained from Deutsch Sammlung von Mikroorganismen, Braunschweig, Federal Republic of Germany. Bacteria were grown on a complex medium modified from that previously described by Blumentals et al (Blumentals et al, Applied and Environmental Microbiology, 56(7):1992–1998 (1990)) consisting of artificial seawater supplemented with 0.3% tryptone, 0.7% yeast extract, and 0.1% soluble potato starch. Medium was prepared and dispensed into two liter bottles and then autoclaved. Following sterilization, in addition to the supplemental salts described previously, elemental sulfur and sodium sulfite were added at 156 mM and 2 mM, respectively. Prior to cooling to below 90° C., the medium was sparged with nitrogen, 1% volume of inoculum from a previously grown culture was added, and the bottles were sealed. The cultures were allowed to incubate at 98° C. in a constant temperature oven for 16 hours and were subsequently harvested. Typical volume of growth medium used for each incubation was 20 liters, providing cell yields of 0.7 to 1.0 g/liter (wet weight).

Standard Enzyme Assay

The dextrinizing activity of the α-amylase was determined using a modification of the assay of Manning and Campbell (Manning et al, J. Biological Chem. 236(11):2952–2957 (1961)). To 20 μl of sample were added 20 μl of 1% soluble starch and 20 μl of 100 mM sodium phosphate, pH 7.0. Controls were prepared using an equal volume of the appropriate buffer in place of the enzyme solution. The samples were incubated at 92° C. for 10 minutes and the reaction terminated by cooling in ice water. Color was developed by the addition of 15 μl of an iodine solution (4% KI, 1.25% I). An additional 1 ml of distilled water was added to each sample to dilute the color of the sample to a measurable range. The absorbance was read at 600 nm with a Pharmacia LB Ultraspec III Spectrophotometer. One unit of α-amylase activity was defined as the amount of protein which hydrolyzed 1 mg of starch per minute.

SDS-PAGE

Electrophoresis under denaturing conditions was carried out on a Pharmacia Phastsystem, using preprepared 8–25% gradient gels (Lot No. QK12892) and SDS buffer strips (Lot No. QL13090). Separation was carried out using the optimized program detailed in the Phastsystem Separations Technique File No. 110 as found in the systems manual.

Native-PAGE

Native gel electrophoresis was carried out according to the method of Laemmli (Laemmli, Nature, 227:680–685 (1970)), excluding the presence of SDS. Polyacrylamide gels were prepared with 0.75 mm thickness and consisted of 8% acrylamide with a 4% stacking gel. Gels were run in a Bio-Rad Mini-protean II apparatus at 25 mA constant current until the bromphenol blue tracking dye reached the bottom of the gel.

For Coomassie blue staining, the gels were soaked for 30 minutes in 0.1% Coomassie blue R-250, 50% methanol, 10% acetic acid and subsequently destained in 50% methanol, 10% acetic acid.

Gels were silver stained using a modification of the method of Morrissey (Morrissey, Anal. Biochem. 117:307–310 (1981)). The gels were prefixed in 50% methanol, 10% acetic acid for 30 minutes, followed by 10% methanol, 10% acetic acid for 30 minutes. Without rinsing, the gels were soaked for 5 minutes in 0.5 mg/ml dithiothreitol followed by a one minute rinse in distilled water. A 0.5% silver nitrate solution was then added and the gel was allowed to soak for 15 minutes. The gels were then rinsed once rapidly in water and once rapidly in developer (100 μl of 37% formaldehyde in 250 ml of 2.5% sodium carbonate), then allowed to soak in developer until the desired level of staining was achieved. The reaction was stopped with a 5% acetic acid solution in which the gels remained for storage.

Activity staining was accomplished by the incorporation of starch into the acrylamide matrix of the resolving gel. When preparing the gels, as described above, 0.05% soluble starch was used in place of distilled water when the gels were cast. To observe the thermophilic amylase activity following electrophoresis the spacers and the gel left between the glass plates were sealed with Saran Wrap to prevent dessication. The gel, between the plates, was then incubated for 30 minutes at 98° C., then stained with iodine solution (see above). The band containing the α-amylase appeared as a clear area in the blue background of the gel. Following this procedure it was still possible to stain the gel with Coomassie blue to visualize the proteins within the gel.

Isoelectric Focusing

The isoelectric point was determined by isoelectric focusing using the Pharmacia PhastSystem electrophoresis apparatus. A preprepared pH 3–9 isoelectric focusing gel (Lot QM 13303) was used. Calibration was accomplished using a Pharmacia Isoelectric Focusing Calibration Kit. Separation was carried out with the optimized method described in the PhastSystem Separation Technique File No. 100 as found in the system manual.

Purification of α-Amylase from *P. furiosus*

(A) Crude Extract. Cells were harvested from growth media at 7,000 Xg for 10 minutes (8000 RPM in a Beckman JA10 rotor). The supernatant was decanted and the pellet collected. The cells from 20 liters of growth medium were resuspended in a final volume of 15 ml of 50 mM sodium phosphate, pH 5.5, and subsequently disrupted by sonication using a Sonifier Cell Disrupter, at 50% duty, intermittently for three minutes. The cytosolic fraction of the lysate was collected after ultracentrifugation at 95,000 Xg for 1 hour (35,000 RPM in a Beckman Ti 45 rotor). All subsequent purification procedures were carried out at room temperature; protein solutions were stored at 4° C.

(B) Ion Exchange #1. The cytosolic fraction was applied to a Q-sepharose column (1.5 cm in diameter with a bed height of 45.5 cm) preequilibrated with 50 mM sodium phosphate pH 5.5 (Buffer A). Under these conditions, the amylase activity bound to the column and was subsequently eluted using 50 mM sodium phosphate pH 5.5, 1M NaCl (Buffer B) with a 200 minute linear gradient (100% A to 100% B). Fractions were collected and the tubes containing amylase were identified by activity and pooled.

(C) Ion Exchange #2. The pooled sample was diluted with an equal volume of buffer A and reapplied to the column which had been reequilibrated with 85% buffer A, 15% buffer B. The sample was eluted with the buffer described above using a 195 minute linear gradient (85% A, 15% B to 40% A, 60% B). The fractions were again pooled based upon activity and dialyzed overnight against 50 mM sodium carbonate pH 10.3 (Buffer A').

(D) Ion Exchange #3. The dialyzed sample was applied to a Q-sepharose (Pharmacia) column (1.5 cm diameter with a bed height of 46.5 cm) preequilibrated with buffer A' and eluted with 50 mM sodium carbonate pH 5.5, 1M NaCl (Buffer B') utilizing a 200 minute linear gradient (100% A' to 100% B'). Fractions containing amylase activity were collected and pooled. The active pool was then concentrated in Centricon 30 microconcentrators at 3020 Xg (5000 RPM in a Sorvall SS34 rotor), in 20 minute intervals, until the total volume was less than 2 ml.

(E) Electroelution. Purification was completed by electroelution from native-PAGE using the Bio-Rad model 491 Prep Cell. The apparatus was assembled using the 28 mm inner diameter gel tube containing an 8% acrylamide gel, 6 cm in height with a 1 cm, 4% stacking gel prepared as described above. The cooling buffer flow was maintained at 100 ml/min; the continuous elution flow was approximately 1 ml/min. The sample was prepared in 2x native sample buffer and was loaded in a volume less than or equal to 2.5 ml. Electrophoresis was carried out at 40 mV constant current and fractions were collected at 2.5 minute intervals. The elution of the protein was monitored with an Isco flow-through absorbance detector at 280 nm, allowing the correlation of specific fractions collected with the elution of protein bands from the gel. Amylase-containing fractions were detected by activity and screened, using silver stained native-PAGE, for purity. The active fractions, shown to be pure within the level of resolution of the silver stain, were pooled as final product.

Protein Quantization

Protein concentration was determined using the Bio-Rad microprotein determination assay, following the manufacturers specifications, with BSA as a standard. Using concentration data obtained with the above method, extinction coefficients were calculated at 254 and 280 giving values of 0.883 and 1.717, respectively.

Size Exclusion Chromatography

The apparent molecular weight of the purified enzyme, under various conditions, was determined on a precalibrated Superose 12 column using a Pharmacia FPLC. Protein was dialyzed against an appropriate buffer to provide the varied conditions desired, and sized in a 1 ml volume at 0.5 ml/min.

Chelation of Divalent Cation and Determination of Free $Ca^{++}$ Concentration A solution containing 35 μmg/ml of purified *P. furiosus* α-amylase in electroelution buffer was depleted of divalent cations by passing it through a Bio-Rad Chelex 0.25 mm ion exchange membrane syringe filter. Free $Ca^{++}$ concentration of the filtered sample was determined by fura-2 fluorescence following the technique of Grynkiewicz et al (Grynkiewicz et al, J. Chromatog. 105: 388–390 (1985)). For the determination of the free $Ca^{++}$ concentration in the sample used for metal ion experiments the buffer $K_D$ is estimated at 200 nM, the $R_{max}$ was determined in 1 mM $Ca^{++}$, and the $R_{min}$ determined in 5 mM EGTA.

Substrate Binding

Enzyme binding of substrate was quantitated by the adsorption of protein in solution to insoluble starch. 50 mg of starch was suspended in 220 μl of a 180 μl of a 180 μg/ml solution of purified α-amylase and incubated at the desired temperature for 15 minutes. The substrate was sedimented by centrifugation, in a microcentrifuge, and the supernatant activity was compared with control values to determine the quantity of protein bound.

Substrate Specificity

Substrate specificity of the enzyme was studied using purified amylase at a concentration of 350 μg/ml in a standard activity assay as described above. Starch and other polysaccharides of various length were incubated with the enzyme to determine the minimum glucopolymer chain length that could act as substrate and the ultimate products of cleavage. Incubations were carried out at 92° C. for 15 minutes. The pattern for hydrolysis was examined by thin-layer chromatography using the method of Hansen (Hansen, J. Chromatog. 105:388–390 (1975)).

Analytical Ultracentrifugation

Analytical ultracentrifugation was carried out using a Beckman Instruments Model E analytical ultracentrifuge with a scanning adsorption optical system interfaced to an acquisition computer by means of a 12-bit Metrabyte DAS-8 analog to digital board. Scanning was carried out in the rapid scan mode; 90,000 data acquisitions were made in the 18 seconds required for the scan. These were averaged in groups of 100 and the actual data density was 425 of these averaged points per centimeter of radius in the centrifuge cell (Lewis, Cambridge, Royal Society of Chemistry, 1992). Initial data conversion and editing was accomplished using software specifically written for this purpose. Further editing and data analysis by mathematical modeling using non-linear least-squares curve-fitting were performed using MLAB (Civilized Software, Bethesda, Md.) operating on the acquisition computer.

Hydrogen Exchange

A stock solution of tritiated water was obtained from New England Nuclear (Boston, Mass.) with a specific activity of 1 mC/ml (Lot 1258-250). 50 μl of tritium stock was added to 100 μl of purified α-amylase at 100 μg/ml in 50 mM sodium phosphate, pH 7.5. The samples were placed in microcentrifuge tubes and incubated at 24° C. and 95° C. At time points of 2 hours and 24 hours, the protein was separated from the tritiated water by size exclusion. This was accomplished using disposable NAP-5 columns (Pharmacia) under the conditions recommended by the manufacturer.

To determine the rate of hydrogen exchange out of the protein a 0.5 ml aliquot of the protein, following size exclusion as described above, was incubated at either 24° C. or 95° C. for two hours and the size exclusion process repeated.

Samples were prepared from the void volume when analyzing the exchange rate into the protein, and both void and inclusion volumes when analyzing the exchange rate out of the protein. To prepare suitable samples, 50 μl of sample was added to 3 ml of Opti-Fluor liquid scintillation fluid (Packard Instrument Co.). Counting was done in an LKB 1212 Rackbeta Liquid Scintillation Counter for one minute intervals.

Fourth-Derivative UV Spectrophotometry

Fourth derivative UV spectra were obtained using a Beckman DU-70 spectrophotometer equipped with a thermally jacketed stage. Absorption readings were taken every 0.5 nm from 240 to 350 nm. The fourth derivatives were calculated numerically with the $\Delta\lambda$ being 12, the results interpreted on a scale of 0.01 to −0.01 absorbance units. The sample used for spectrum generation contained 350 μg/ml purified amylase in 50 mM Hepes buffer, pH 7.0.

Fluorescence Spectroscopy

Temperature effects on fluorescence intensity and fluorescence emission spectra were recorded on an SLM 8,000 spectrofluorometer. Excitation wavelength used was 290 nm and fluorescence intensity was measured at 350 nm. The band wavelength was 8 nm. The sample utilized was identical to that used in fourth-derivative measurements.

Amino Acid Analysis

Protein samples were hydrolyzed in constant boiling HCl (No. 24309 Pierce Chemical Co.) containing 0.1% phenol at 110° C. for 24 hours. Amino acids were analyzed using a Waters HPLC system and Pico-Tag™ derivitization on a 3.9×300 mm Pico-Tag column (No. 10950 Waters, Division of Millipore). Postcolumn detection was carried out at 254 nm on a Model 440 Waters detector.

Cystine content was determined by performic acid oxidation and quantitization of cysteic acid. Purified enzyme was dissolved in 100 μl of 88% formic acid and cooled to 0° C. To this sample was added 100 μl of performic acid reagent (10 ml formic acid+1 ml fresh 30% $H_2O_2$+0.1 ml 90% phenol in $H_2O$; allowed to sit 1 hour at room temperature, cool to 0° C.). After incubation on ice for one hour, the hydrolysis was completed as described above.

Protein Sequence Analysis

Purified enzyme was digested with cyanogen bromide and, following reduction and pyridylethylation, with trypsin, using a modification of the methodology of Stone et al (Stone et al, Academic Press, N.Y.: 33–47 (1989)). The resulting fragments were then separated by gradient elution from 100% water containing 0.1% (v/v) trifluoroacetic acid (TFA) to 70% acetonitrile containing 0.1% (v/v) TFA on an Aquapore RP-300 reverse phase narrow-bore column (0.2 cm×25 cm), utilizing a Dionex Al-450 BioLC system.

Amino acid sequence analysis was performed on a Porton instruments Model 2020 off-line sequencer using standard program #1. PTH amino acid analysis was carried out on a Beckman Gold system using a modified sodium acetate gradient program and a Hewlett-Packard narrow-bore C-18 column.

Effect of Temperature on Buffer pH

The pH of the buffers used were calibrated for accuracy at the temperatures used for the respective measurements.

EXAMPLE 1

Purification of α-Amylase

In order to purify the amylase, crude cell supernatant was applied, then eluted from three successive ion exchange columns as described above. The apparent molecular weight and the relative purity of the protein were monitored throughout the purification process using activity staining in conjunction with Coomassie staining. Following the third ion exchange column, the obtainable separation on native-PAGE of the proteins remaining in solution made electro-elution a viable option for production of purified protein. A summary of the purification is provided in Table 1 and FIG. 1.

TABLE 1

Purification Summary of Amylase from *Pyrococcus furiosus*

| Step | Vol (ml) | Total Activity U | Total Protein (mg) | Specific Activity | Purifi-cation | % Yield |
|---|---|---|---|---|---|---|
| Crude Extract | 11.0 | 35.288 | 1100.94 | 0.032 | 1.0 | 100 |
| Ion Exchange #1 | 40.0 | 76.000 | 99.90 | 0.761 | 23.8 | 100 |
| Ion Exchange #2 | 42.5 | 49.717 | 21.83 | 2.334 | 72.9 | 65 |
| Ion Exchange #3 | 15.0 | 19.758 | 6.11 | 3.234 | 101.1 | 26 |
| Electroelution | 10.0 | 4.802 | 0.43 | 11.299 | 353.1 | 6.3 |

Figure 1B:
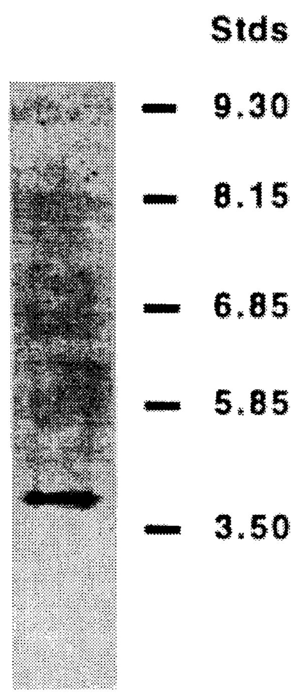

The isoelectric point of the enzyme, as determined by isoelectric focusing, was found to be approximately pH 4.3 (FIG. 1B).

EXAMPLE 2

Physiochemical Properties

Figure 2A:
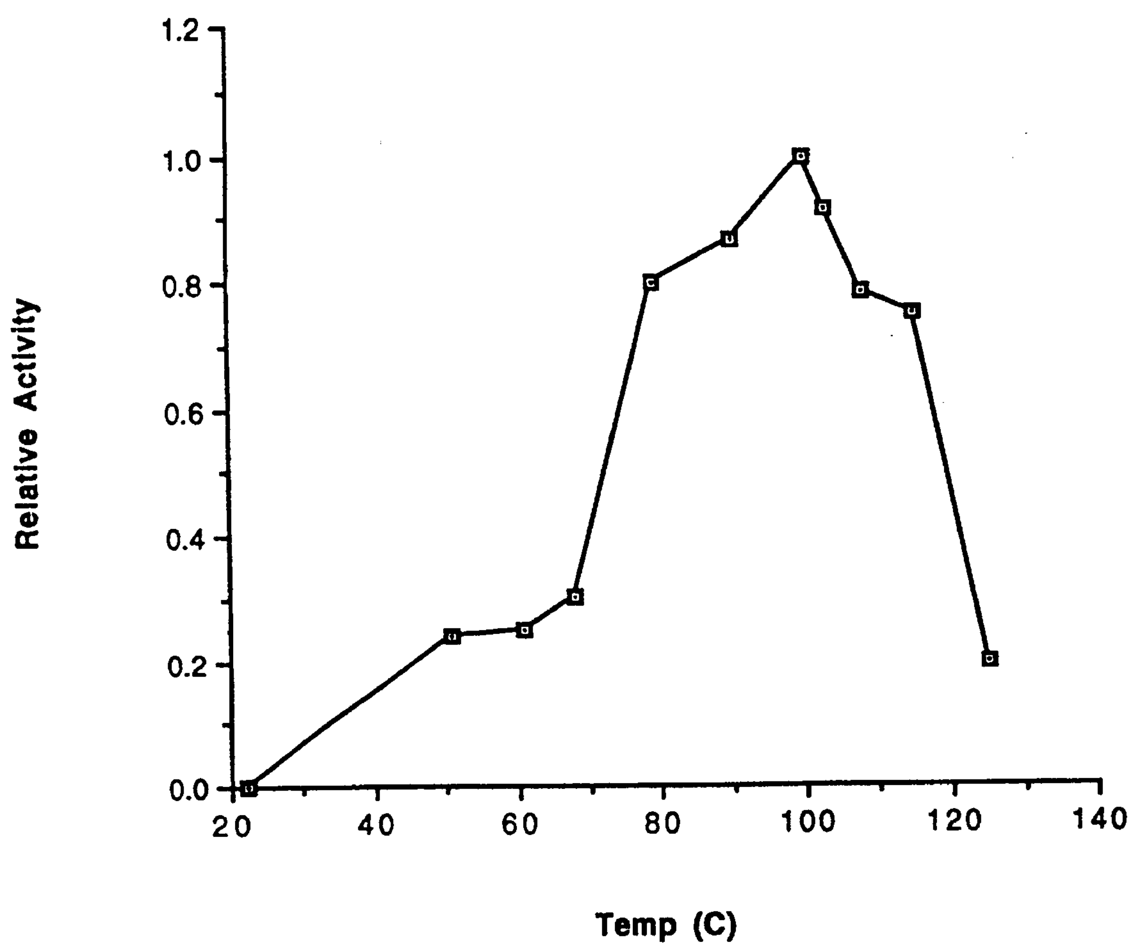
FIG. 2: Characteristics of *P. furiosus* amylase activity. (A) The effect of temperature on amylase activity. Activity was assayed at different temperatures using the standard activity assay. Incubation was for 10 min at pH 7.0. (B) Thermostability of enzymatic activity. The amylase samples were incubated at 100° C. for various time intervals then the relative activity was determined compared with a non-incubated sample using the standard activity assay. (C) The effect of pH on amylase activity. The relative enzyme activity was determined at varying pH using the standard activity assay (pH was maintained using 100 mM sodium phosphate adjusted to the appropriate value).
Figure 2B:
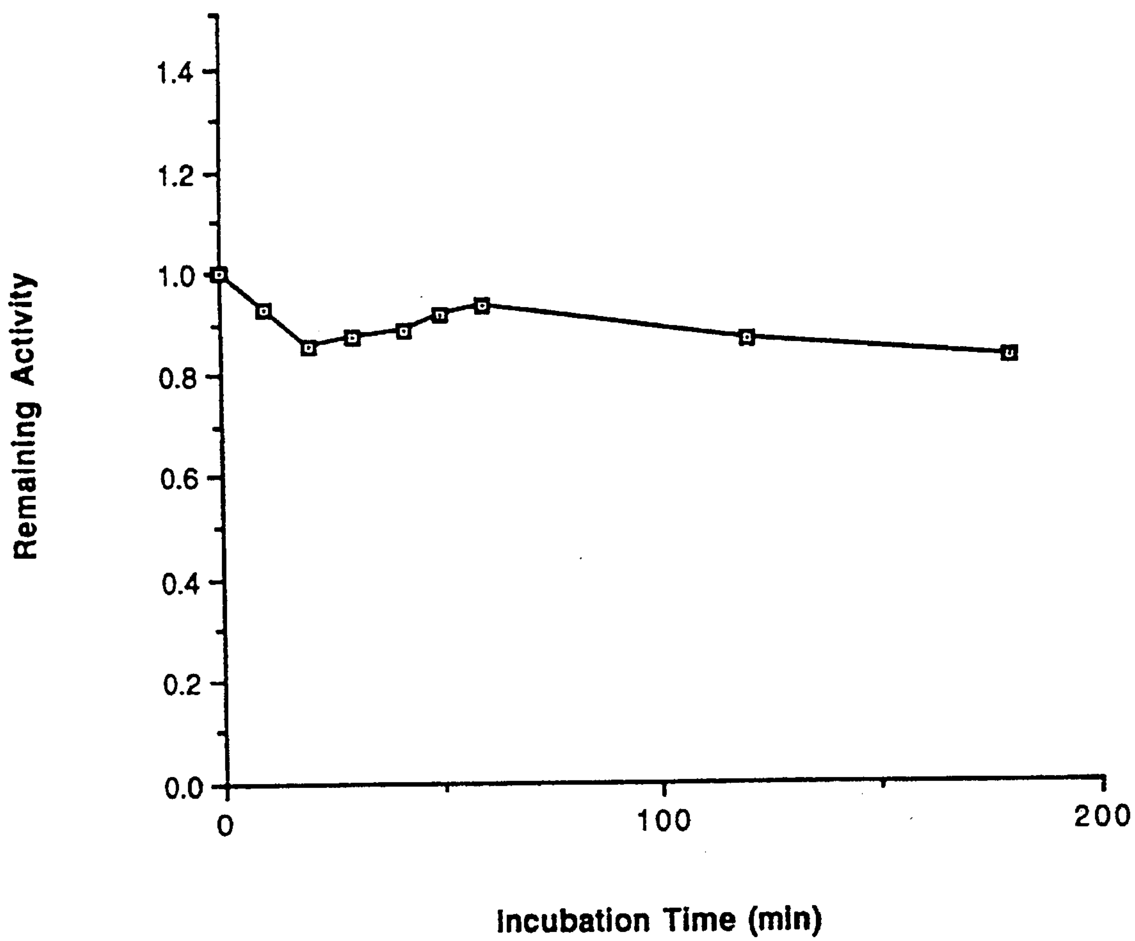
Figure 2C:
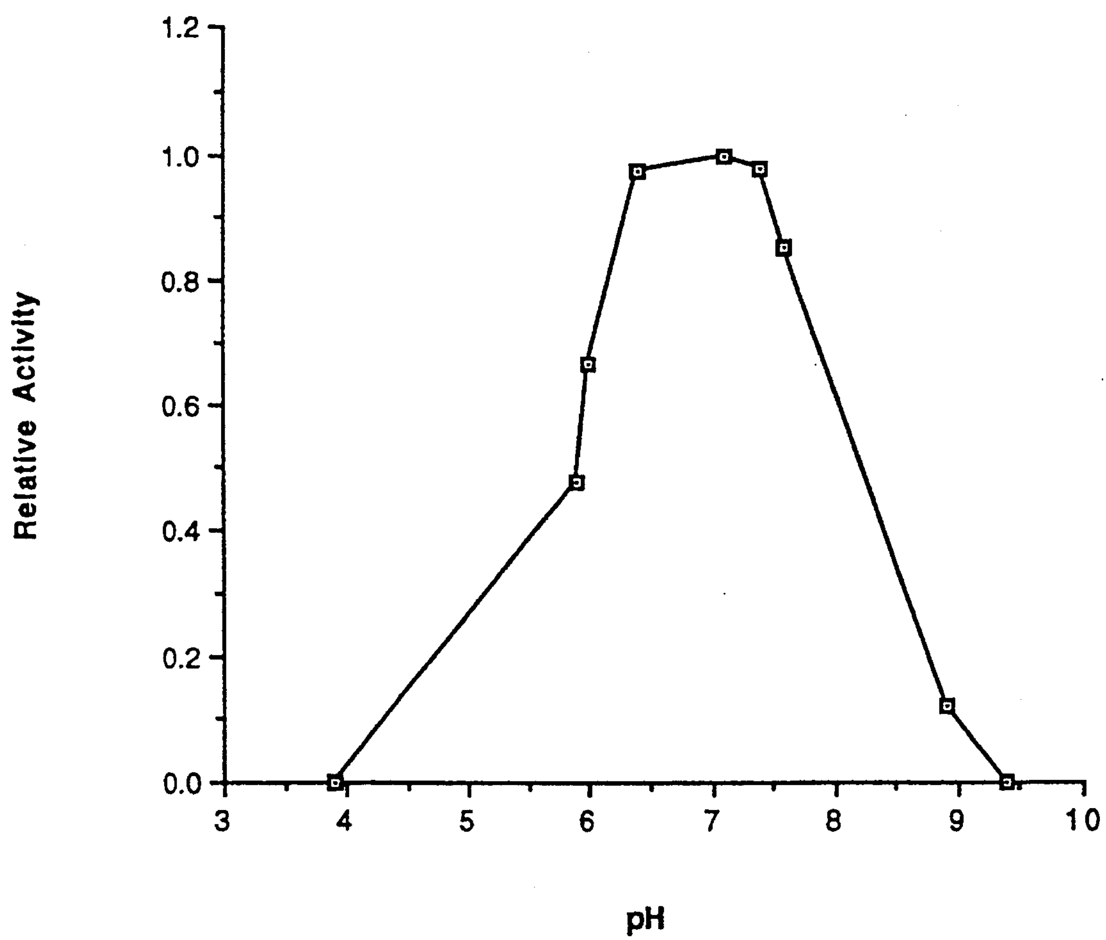

The purified enzyme displays optimal activity at 100° C. with an onset of activity at approximately 40° C. and a substantial loss of activity at 120° C. Within the temperature range of *Pyrococcus furiosus* growth, the purified amylase exhibits activity at the level of 80% of optimum or higher (FIG. 2A). The thermostability of activity at the temperature of optimum activity (100° C.) was found to be relatively constant over the interval tested (FIG. 2B). The pH optimum, determined at the optimal temperature, was found in a pH range from 6.5 to 7.5 with a rapid decline in activity as pH moved to either extreme (FIG. 2C).

Figure 3:
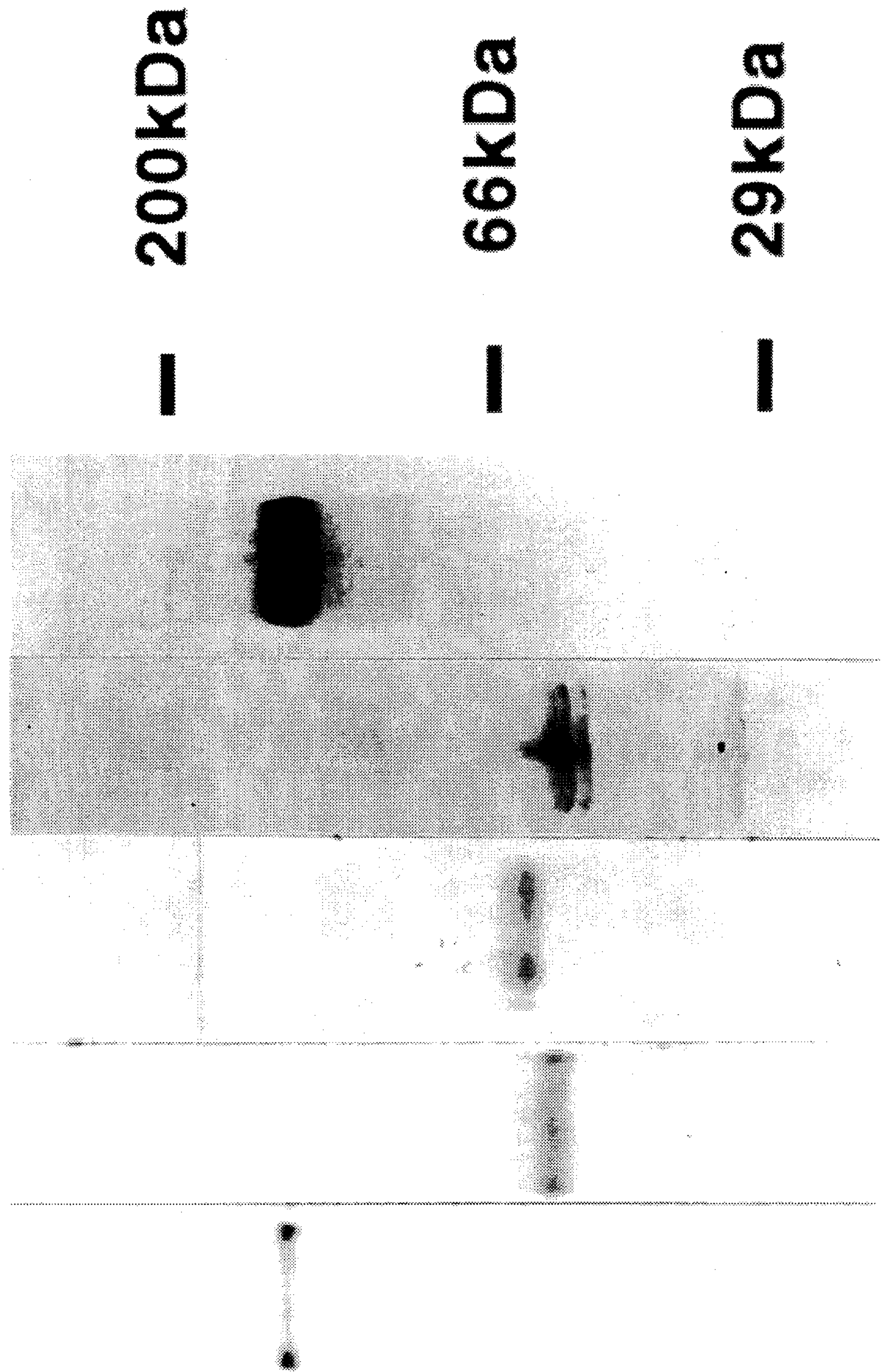
FIG. 3: Electrophoretic characterization of *P. furiosus* amylase. Lane: 1, Native polyacrylamide electrophoresis; 2 and 3, electrophoresis in the presence of 8M urea with and without sample heating, respectively; 4 and 5, SDS polyacrylamide electrophoresis with and without sample heating respectively.

The molecular mass and subunit composition of the purified enzyme were determined by size exclusion chromatography under various conditions, analytical ultracentrifugation, and both native and SDS-polyacrylamide gel electrophoresis. Evaluated within a range of pH from 7.0 to 10.3, the apparent molecular mass of the protein as determined by gel filtration was found to be 157±15 KDa (data not shown). An increase in the ionic strength up to 1M had no significant effect on the apparent molecular mass as determined by size exclusion. A summary of electrophoretic analysis is shown in FIG. 3. When analyzed using native-polyacrylamide gel electrophoresis, the apparent molecular mass was 129 kDa, regardless of sample heating, based on comparison with the migration of β-amylase, bovine serum albumin, and carbonic anhydrase. Electrophoresis in the presence of 8M urea yields a shift in molecular weight of 66 kDa, with a slight shift in molecular weight associated with denaturation when the sample is heated. This suggests that the protein is a homogenous dimer which is dissociated in the presence of 8M urea, the individual subunits of which are not completely denatured until heated. SDS-polyacrylamide gel electrophoresis, when performed without heating the sample prior to loading, yields results identical to those observed under native conditions. When the sample was heated in the presence of SDS thermal breakdown was observed, the extent of which was dependent on the duration of boiling (data not shown). This thermal instability in the presence of SDS is similar to that which has been observed with other thermophilic enzymes from hyperthermophilic archaebacteria (Pihl, J. Bacteriology, 173(6):1839–1844 (1991)).

Ultracentrifugal equilibrium at 10,000 rpm and 20° C. was verified as attained by 113 hours. The value of φ', the apparent compositional partial specific volume, was calculated from the amino acid analysis data using the values of Zamyatnin (Zamyatnin, Palo Alto, Annual Reviews, Inc. (1984)). The value of ρ, the solvent density was calculated from handbook data. The data, in the form of $c_r$, the concentration expressed as absorbance at 280 nm as a function of radial position in the ultracentrifuge cell, was then fit using non-linear least-squares curve-fitting with the equation for a single monomeric thermodynamically ideal species as a mathematical model:

$$c_r = c_b \exp(A\, M\, (r^2 - r_2^2)) + e$$

Here, $c_b$ is the concentration at the cell bottom, $r_b$; M is the molecular mass; $A=(1-\phi'\rho)w^2/2RT$ where w is the angular velocity of the rotor in radians per second, R is the gas constant; and T is the absolute temperature; e is a baseline error correction term. The fitting parameters are M, $c_b$ and e.

Figure 4A:
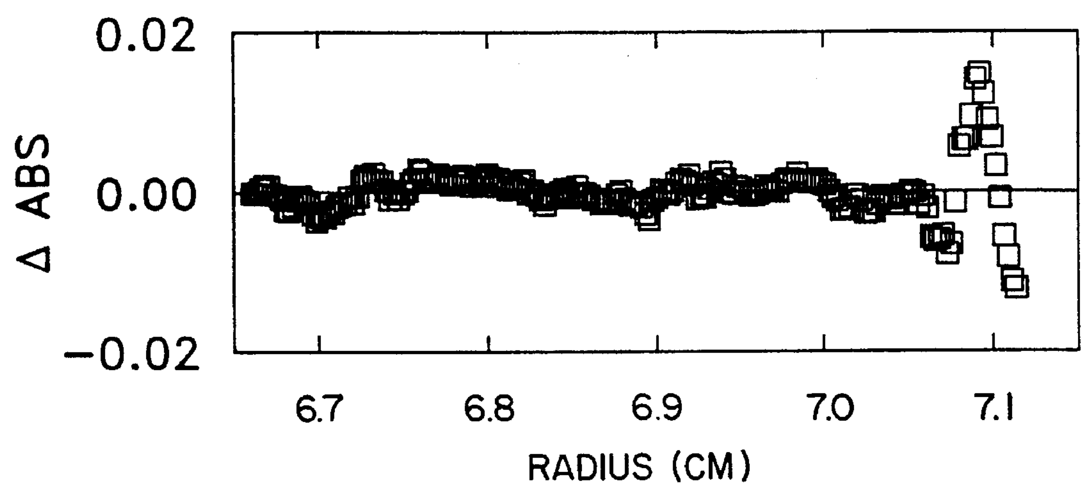
FIG. 4: Alpha-amylase at ultracentrifugal equilibrium after 113 hours at 1000 rpm and 20° in 50 mM potassium phosphate buffer, pH 8.0. Lower panel (FIG. 4B): concentration distribution as a function of radial position in the ultracentrifuge cell. Upper panel (FIG. 4A): Distribution of the residuals about the filling line. There is no apparent systematic deviation and the quality of fit is quite good. The value of the RMS error is $2.34\times10^{-}$absorbance units at 280 nm.
Figure 4B:
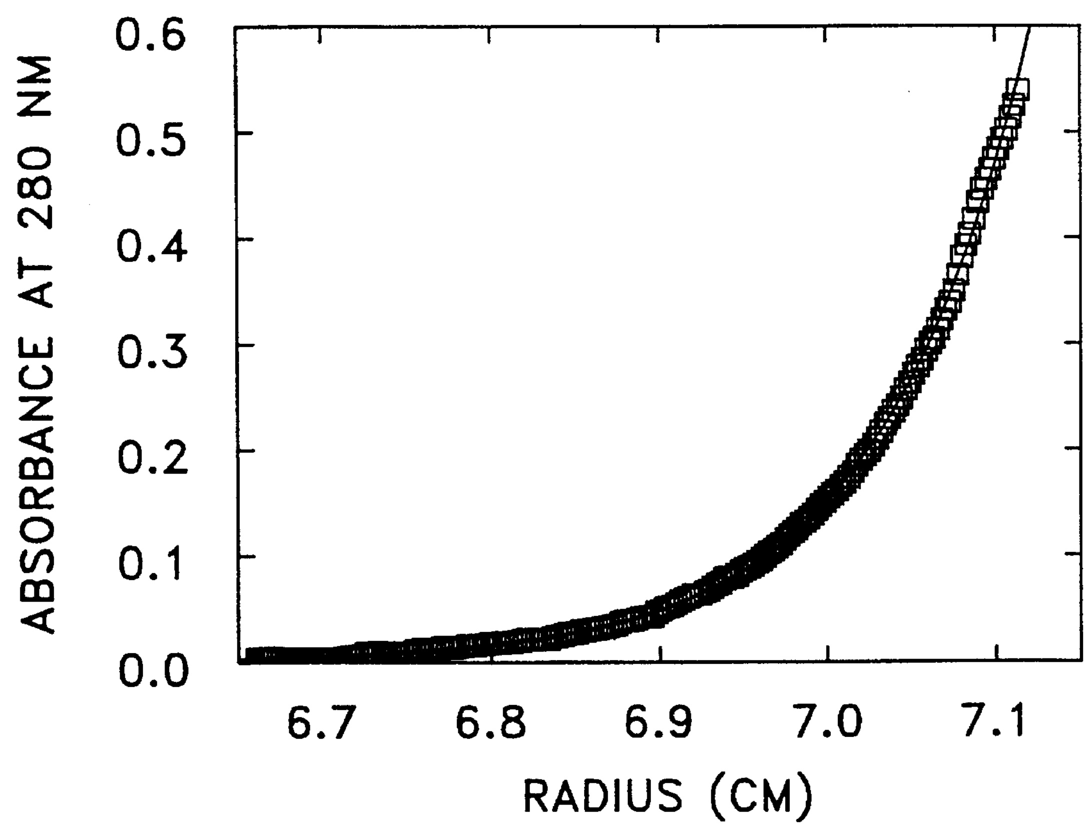

Using this equation as a mathematical model for weighted non-linear least-squares curve-fitting, a value for the molecular mass of 130,500 was obtained. There was no evidence of heterogeneity or non-ideality. From the standard error estimates returned in the fitting procedure and from preliminary studies of the-standard error using the bootstrap technique (Efron, Soc. for Ind. and App. Math. (1982)) an error estimate of ±550 is probable. The results of the fitting are shown in FIG. 4.

Figure 5:
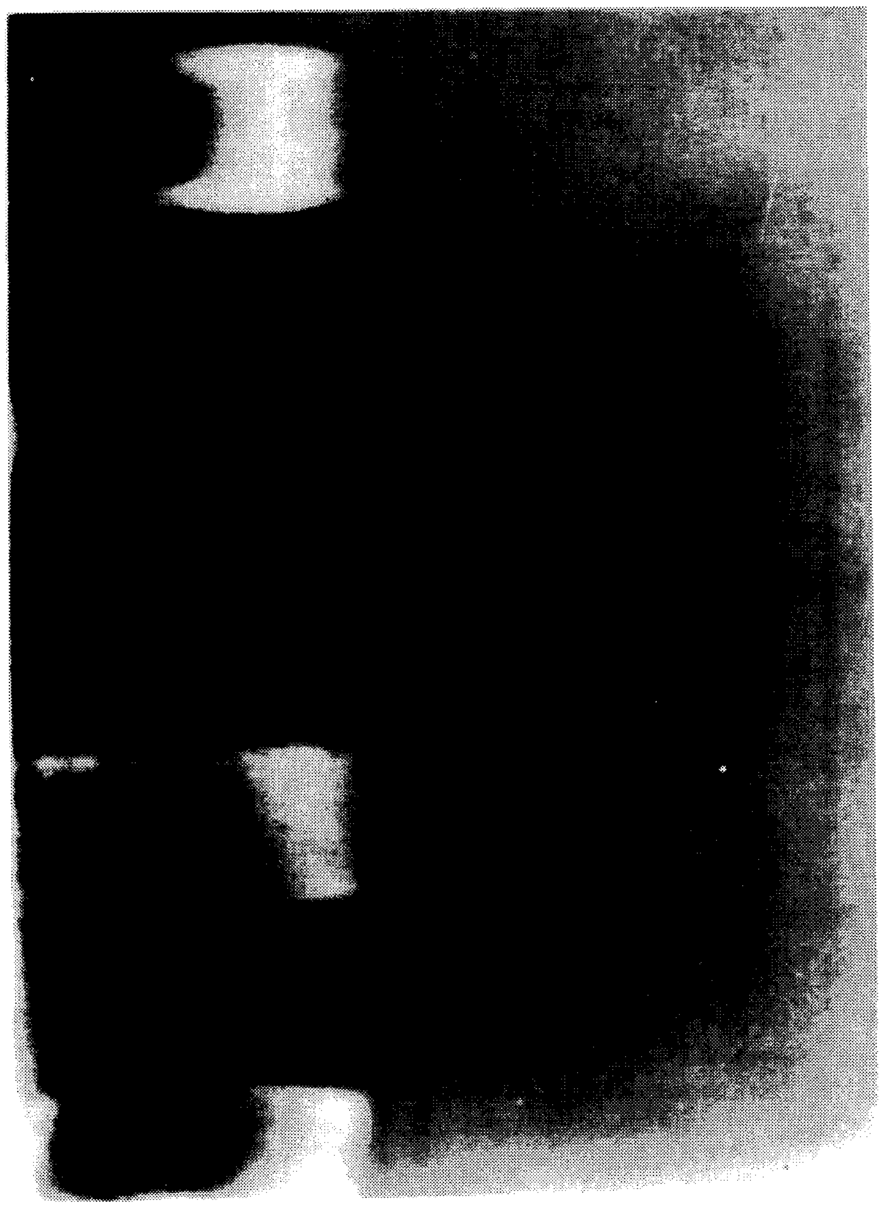
FIG. 5: The effect of denaturants and metal ions on activity stained native polyacrylamide electrophoresis. Samples were heated 15 min in the following: Lane 1, 100 mM sodium phosphate pH 7.0; Lane 2, 5 mM EDTA; Lane 3, % SDS; Lane 4, 12% β-mercaptoethanol. The samples were run on a native gel (8% acrylamide), containing 0.02% starch, and stained as described in the Examples.

To determine the effect of denaturants and metal ions on the activity of *P. furiosus* α-amylase activity, stained native-PAGE or in vitro activity assays were utilized. Analysis by native-PAGE in which samples were heated for 15 minutes in the presence of either 5 mMEDTA, 2% β-mercaptoethanol, or 1% SDS indicated that EDTA and β-mercaptoethanol, at these concentrations, had no significant effect on activity while, with 1% SDS, the loss of activity was almost complete (FIG. 5). These results could not be repeated using a standard activity assay due to interference caused by the aforementioned compounds.

The extent of activity loss induced by the denaturants, urea and guanidine HCl, was determined using a standard activity assay in which the above-mentioned reagents were present in 1M concentrations. At 98° C. the residual activity in the presence of these denaturants was 86.5% and 73% for urea and guanidine HCl, respectively.

The effect of free $Ca^{++}$ and other metal ions on amylase activity was determined using an enzyme solution depleted of free calcium and other divalent cations. The measured concentration of free calcium in the purified sample was found to be less than 100 nM. Activity was then measured in the presence of a variety of divalent cations at different concentrations. With the exception of $Ca^{++}$, the addition of all of the metal ions tested caused enzyme inhibition (Table 2). The addition of free calcium caused a slight stabilization of the enzyme, the extent of which was constant over the range of concentrations tested.

TABLE 2

THE INFLUENCE OF METAL IONS ON THE PERCENT ACTIVITY FROM *P. FURIOSUS* AMYLASE

| | Concentration (mM) | | | |
|---|---|---|---|---|
| Metal Ion | 0 | 1 | 2 | 3 |
| Ca | 100 | 108 | 109 | 108 |
| Co | 100 | 48 | 6 | 6 |
| Cr | 100 | 27 | 0 | 0 |
| Cu | 100 | 56 | 6 | 6 |
| Fe | 100 | 7 | 0 | 0 |
| Mg | 100 | 45 | 46 | 45 |
| Zn | 100 | 39 | 3 | 3 |

Percent activity was determined using the standard activity assay supplemented with metal cation solutions to give the final concentrations shown. Metal cations were prepared in 100 mM sodium phosphate pH 7.0

The ability of the purified amylase to bind substrate was assessed at a number of temperatures below the range of enzymatic activity. When measured as a function of activity bound to insoluble substrate, a loss of less than 4% of the total enzymatic activity was found at 4° C., 21° C., and 37° C.

Kinetic experiments were carried out using the standard activity assay at a variety of temperatures. The pH was maintained at 7.0 corresponding to the enzymatic activity maximum. Values for $k_m$ and $V_{max}$ were obtained from Lineweaver-Burk plots and are summarized in Table 3. At 65° C. and 75° C. similar results were obtained for $k_m$. When the temperature was increased to 91° C. the $k_m$ decreased approximately 50%.

TABLE 3

TEMPERATURE DEPENDENCE OF THE KINETIC PARAMETERS OF THE AMYLASE FROM *P. FURIOSUS*

| Temp (C.) | Km (mg/ml) | Vmax (mg/min/mg enz) |
|---|---|---|
| 65 | 6.84 | 34.24 |
| 75 | 6.85 | 37.45 |
| 91 | 3.69 | 20.00 |

EXAMPLE 3

Substrate Specificity

Figure 6:
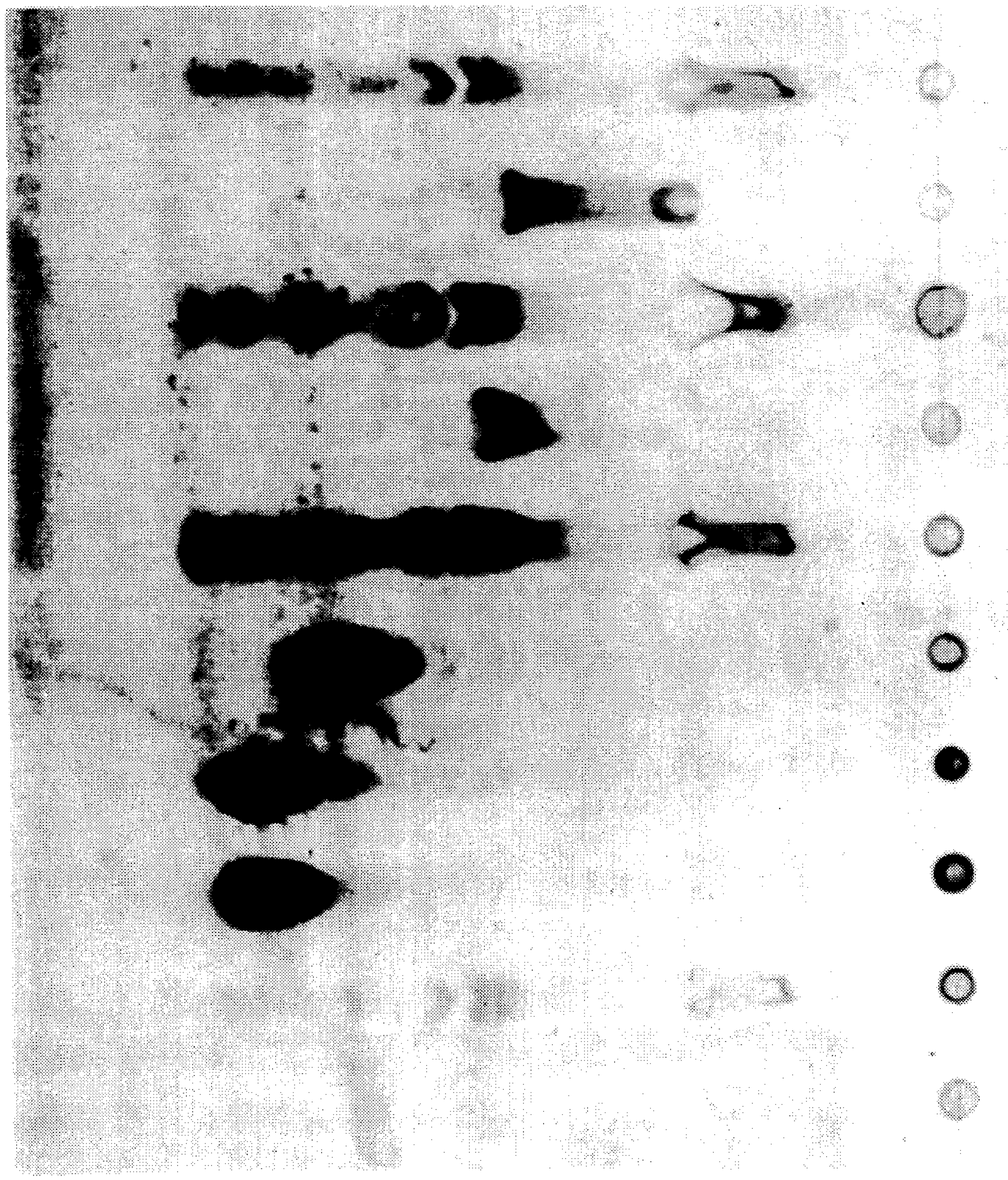
FIG. 6: Substrate specificity of the purified amylase from *P. furiosus*. The products resulting from standard activity assay reactions with starch and various polysaccharides as substrates are presented. Initial substrate concentration was 1% (w/v), the reactions were allowed to incubate 15 min at 92° C. Lanes: 1 and 2, starch (without and with enzyme respectively); 3 and 4, maltose; 5 and 6, maltotriose; 7 and 8, maltohexaose; 9 and 10, maltoheptaose.

The action of purified amylase on starch and various polysaccharides is shown in FIG. 6. Starch was digested to the level of glucose and maltose in addition to a mixture of polysaccharides, a majority of which were maltotetraose (G4), maltopentaose (G5), and maltohexaose (G6). In the presence of shorter polysaccharides, the enzyme displays equilibrium-dependent product formation favoring the previously enumerated polysaccharides (G4, G5, G6). With maltose as a substrate there is negligible enzymatic activity, limited to the production of a small quantity of maltotetraose and maltohexaose. The amylase cleaves maltotriose to glucose and maltose, in addition to formation of G4, G5 and G6. Patterns similar to those obtained with maltotriose were obtained when maltohexaose and maltoheptaose (G7) were used as substrate. The evidence suggests that, although maltotriose (G3) can be cleaved by the enzyme, the final equilibrium also mirrors the reverse reaction, producing longer polysaccharides.

EXAMPLE 4

Amino Acid Composition and Protein Sequence Analysis

The results obtained from amino acid analysis did not show any significant differences from the compositions of the enzyme of other species with markedly differing stabilities (Ihara et al, J. Biochem. 98:95–103 (1985a); Koch et al, Arch. Microbiol. 155:572–578 (1991); Melasniemi, Biochem. J. 50:813–818 (1988); Yang et al, Nucleic Acids Res. 1:237–249 (1983); Yuuki et al, J. Biochem. 98:1147–1156 (1985)) (Table 4).

TABLE 4

AMINO ACID COMPOSITIONS OF AMYLASES FROM *P. FURIOSUS* AND OTHER SOURCES

| | Amino Acid Compositions (residues/100 residues) | | | | | |
|---|---|---|---|---|---|---|
| | *Pyrococcus furiosus* | *Pyrococcus woesei* | *Clostridium thermohydro-sulfuricum* | *Bacillus licheniformis* | *Bacillus stearo-thermophilus* | *Bacillus subtillis* |
| Asx | 5.7 | 10.8 | 15.0 | 12.1 | 11.5 | 16.6 |
| Thr | 3.0 | 7.7 | 8.2 | 5.5 | 8.2 | 7.1 |
| Ser | 4.4 | 5.1 | 6.3 | 5.3 | 5.5 | 8.8 |
| Glx | 13.7 | 8.1 | 9.1 | 9.1 | 6.0 | 8.2 |
| Pro | 7.0 | 4.3 | N.D. | 3.1 | 4.6 | 3.8 |
| Gly | 11.4 | 8.4 | 9.1 | 8.8 | 8.9 | 8.0 |
| Ala | 7.2 | 6.9 | 6.4 | 8.0 | 6.7 | 8.6 |
| Cys | 0.5 | N.D. | N.D. | 0.0 | 0.5 | 0.1 |
| Val | 6.1 | 5.5 | 7.6 | 6.2 | 5.6 | 5.0 |
| Met | 1.5 | 2.0 | 1.6 | 1.6 | 2.2 | 1.7 |
| Ile | 5.7 | 4.0 | 6.6 | 4.1 | 4.2 | 5.3 |

TABLE 4-continued

AMINO ACID COMPOSITIONS OF AMYLASES FROM *P. FURIOSUS* AND OTHER SOURCES

| | Amino Acid Compositions (residues/100 residues) | | | | | |
|---|---|---|---|---|---|---|
| | *Pyrococcus furiosus* | *Pyrococcus woesei* | *Clostridium thermohydro-sulfuricum* | *Bacillus licheniformis* | *Bacillus stearo-thermophilus* | *Bacillus subtillis* |
| Leu | 9.3 | 6.7 | 5.9 | 7.0 | 7.1 | 6.7 |
| Tyr | 3.6 | 5.7 | 7.3 | 6.0 | 6.0 | 4.3 |
| Phe | 5.7 | 4.8 | 4.3 | 4.3 | 5.1 | 3.8 |
| His | 1.7 | 3.4 | 1.4 | 4.9 | 2.7 | 2.6 |
| Lys | 8.9 | 5.7 | 7.8 | 5.8 | 6.0 | 5.0 |
| Trp | N.D. | N.D. | N.D. | 3.3 | 4.0 | 2.1 |
| Arg | 5.1 | 4.6 | 3.5 | 4.7 | 4.9 | 3.8 |
| Molecular mass (kDa) | 130.5 | 63.7 | 330.0 | 58.5 | 62.5 | 72.7 |
| Number of Residues | 1186.0 | 580.0 | — | 512.0 | 548.0 | 660.0 |
| Temperature optimum (C.) | 100.0 | 100.0 | 90.0 | 80–90 | 75–80 | 55.0 |

Eighteen amino acid residues were obtained from the sequencing of the N terminus of the purified protein: G/M-D-K-I-N-F-I-F-G-I-H-N-H-Q-P-L-G-N (SEQ ID NO:3). Following digestion, a segment of internal protein sequence was purified. This fragment had the N terminal sequence: T-L-N-D-M-R-Q-E-Y-Y-F-K (SEQ ID NO:2).

EXAMPLE 5

Hydrogen Exchange

A summary of the hydrogen exchange data is listed in Table 5. Due to the nature of the gel filtration column utilized, the counts incorporated with "fast", "intermediate" and "slow" exchange rates were included in the protein bound fraction. Native protein at ambient and active temperature, 24° C. and 94° C., respectively, displayed a level of incorporation much lower than that observed in urea denatured samples, indicating a low availability of hydrogen atoms for exchange in the native folded conformation. A slight increase in bound tritium was observed when the temperature was maintained at 94° C. When the rate of out-exchange was analyzed, at ambient and 94° C., the exchange was found to be virtually complete after 2 hours. Tritium in exchange at 94° C. followed by out-exchange at ambient temperature resulted in the trapping of 13% of the total counts. This may also be attributed to a temperature dependent increase in the accessibility of exchangeable hydrogens.

TABLE 5

TITRIUM EXCHANGE AS A FUNCTION OF TEMPERATURE IN THE AMYLASE FROM *P. FURIOSUS*

In-Exchange

| Temp (C.) | Incorporation 2 hrs (CPM/ml) | Incorporation 24 hrs (CPM/ml) |
|---|---|---|
| 24 | 7526.6 | 8040 |
| 94 | 9580.0 | 10360 |

Out-Exchange

| Temp of in-exchange (C.) | Temp of out-exchange (C.) | Incorporated counts Remaining (CPM/ml) |
|---|---|---|
| 24 | 24 | 13 |
| 94 | 94 | 0 |
| 94 | 24 | 200 |

EXAMPLE 6

Figure 7:
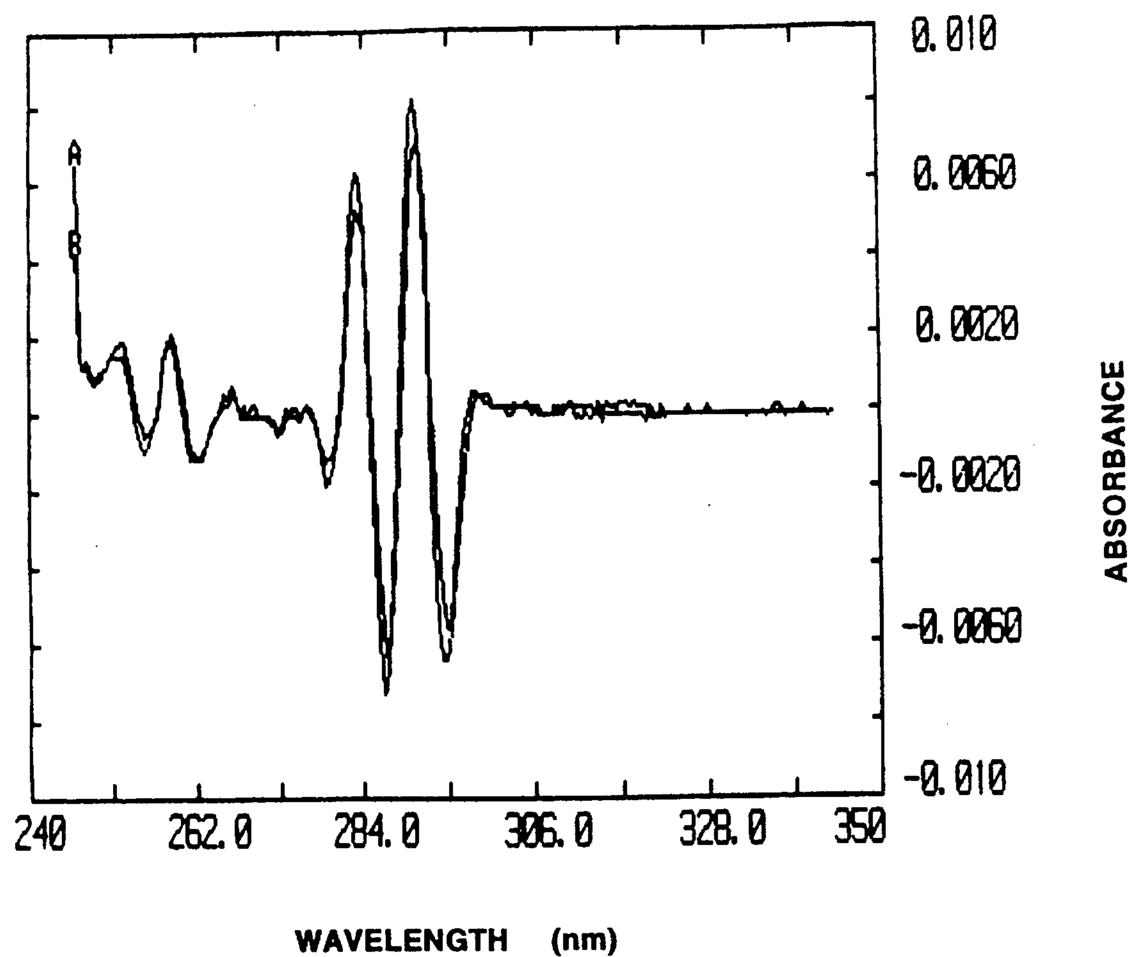
FIG. 7: Fourth derivative UV spectrophotometric analysis of the purified amylase. Parameters of spectrum acquisition are described in the Examples A, spectrum at 85° C.; B spectrum at 26° C.

Fourth-Derivative UV Spectrophotometry and Intrinsic Fluorescence Measurements A series of fourth-derivative spectra were generated at temperatures ranging between 26° C. and 85° C. Over this range there was a gradual reversible red shift, which was temperature dependent. The shift is insignificant in magnitude and is linear as a function of temperature (FIG. 7). This change in spectrum is thought to be a solvent effect rather than an indication of a change in the environment of the constituent aromatic amino acids in the protein.

Figure 8A:
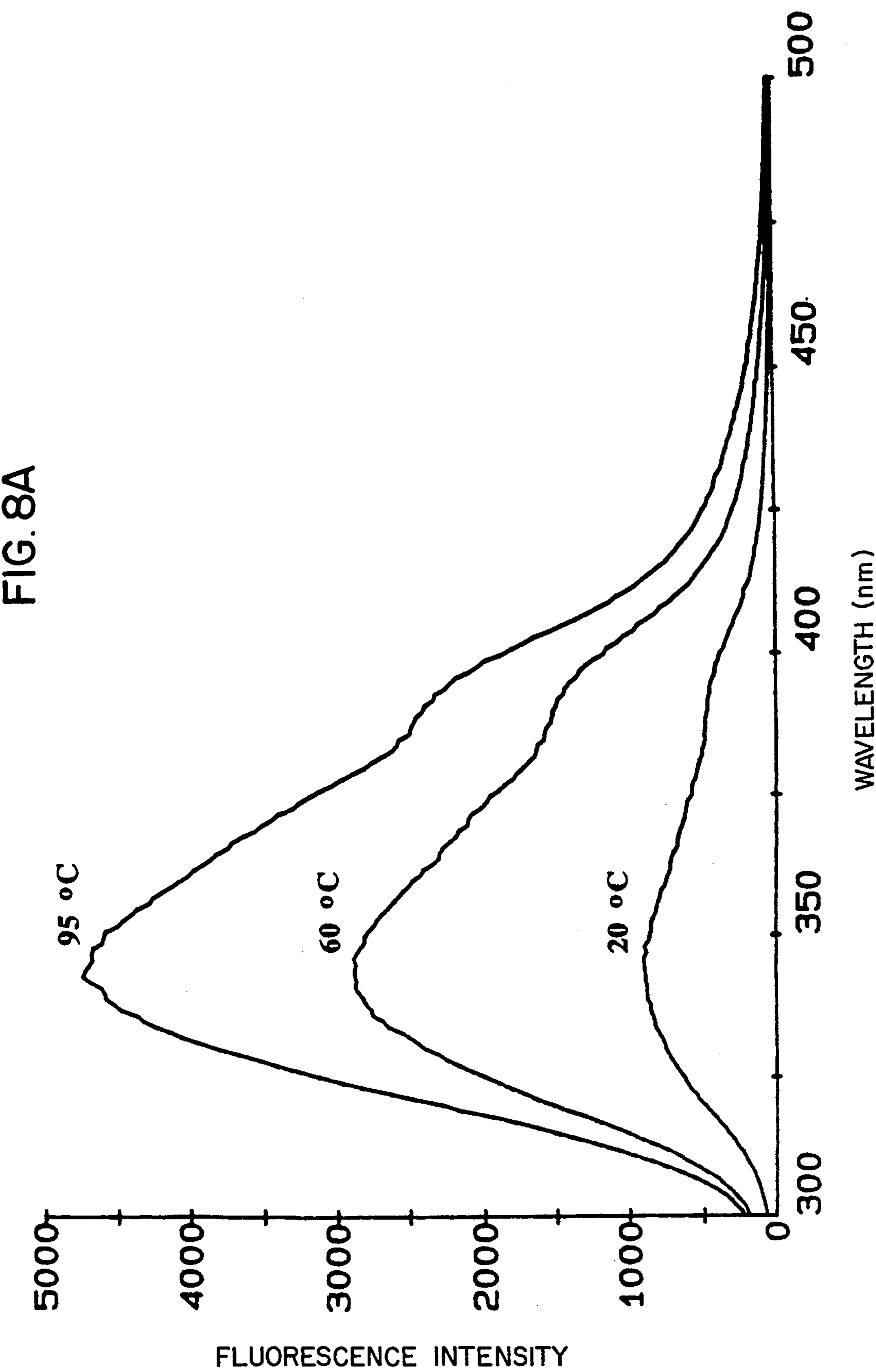
FIG. 8: The effect of temperature on the intrinsic fluorescence of the purified amylase. (A) Comparison of emission spectra at various temperatures. Excitation wavelength was 290 nm, the band wavelength 8 nm. (B) Fluorescent intensity as a function of temperature. Excitation wavelength at 290, emission at 350 nm with a band wavelength of 8 nm.
Figure 8B:
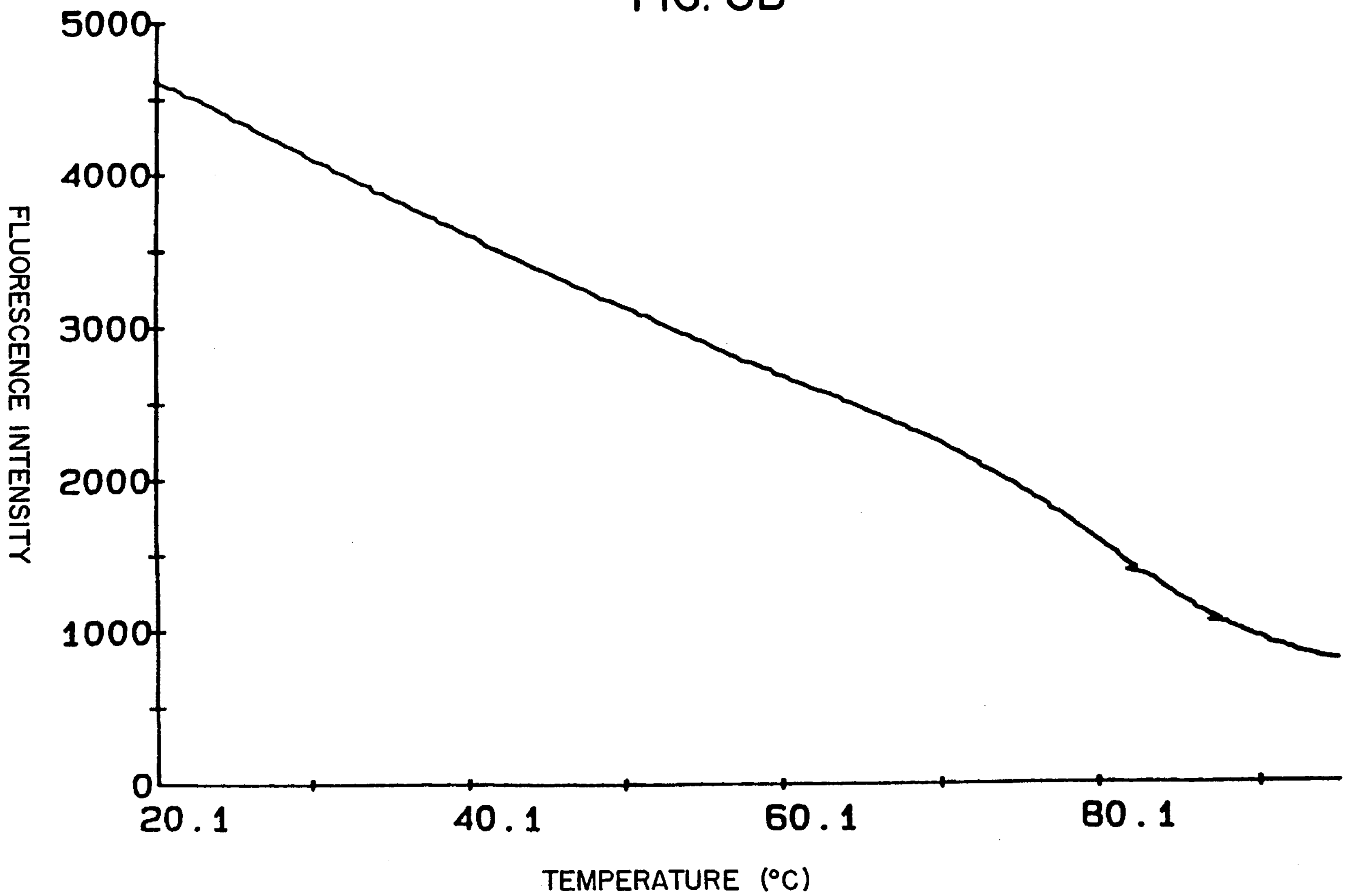

Fluorescence emission of α-amylase from *P. furiosus* 20° C. exhibits a maximum at 345 nM. This maximum indicates that the tryptophan environments at this temperature are relatively polar (Teale, Biochem. J. 76:381–388 (1960)). When the spectrum was monitored over a range of temperatures there was no shift in the wavelength of the emission maximum (FIG. 8A). The maintenance of a constant emission maximum suggests that the tryptophan residues remain in the polar environment independent of temperature. When the fluorescence intensity was examined as a function of temperature it displayed a gradual decrease with a minor transition at approximately 65° C. (FIG. 8B). This transition is indicative of a minor transfer of one or more tryptophan residues to a more polar environment (Ingham et al, J. Biol. Chem. 259(11901–11907): (1984)). The smooth decrease in intensity with temperature reflects increased quenching due to greater thermal motion (Galley et al, Biopolymers Symp. 1:367–381 (1964)). When the intrinsic fluorescence characteristics are considered in concert, it appears that the tryptophan residues in the enzyme are maintained in a polar environment and may shift slightly to a more polar environment at higher temperature, this shift being insufficient to be detected as a shift in emission maximum.

The contents of all references cited herein above are incorporated herein by reference.

One skilled in the art will appreciate from a reading of this disclosure that various changes in form and detail can be made without departing from the true scope of the invention.

What is claimed is:

1. An α-amylase isolated and purified from the cytosol of Pyrococcus furiosus which has the amino acid sequence shown in FIG. 9 (SEQ ID NO:1).

2. A purified polypeptide comprising a sequence of amino acids corresponding to at least 12 contiguous amino acids shown in FIG. 9 (SEQ ID NO:1).

3. An α-amylase isolated and purified from the cytosol of *Pyrococcus furiosus* which hydrolyzes starch and maltotriose;

does not significantly bind substrate at a temperature below that required for activity;

has an optimum pH in the range of 6.5–7.5; and an optimum temperature of about 100° C.

4. The isolated and purified α-amylase of claim 3 wherein said α-amylase has the amino acid sequence shown in FIG. 9 (SEQ ID NO:1).

5. A method of purifying an α-amylase which comprises the steps of:

i) lysing cells of *Pyrococcus furiosus* and isolating a cytosolic fraction therefrom;

ii) applying said fraction to an ion exchange resin under conditions such that said α-amylase binds to said resin;

iii) separating said bound α-amylase from unbound material present in said fraction;

iv) eluting said α-amylase from said resin, whereby a first partially purified α-amylase preparation is obtained; and v) separating α-amylase present in said first partially purified preparation from other proteinaceous material present in said first partially purified preparation by electroelution, whereby purified α-amylase is obtained, and wherein the resulting α-amylase hydrolyzes starch and maltotriose;

does not significantly bind substrate at a temperature below that required for activity;

has an optimum pH in the range of 6.5–7.5; and an optimum temperature of about 100° C.

6. The method according to claim 5 wherein the method further comprises:

iva) applying said first partially purified preparation resulting from step (iv) to an ion exchange resin under conditions such that said α-amylase binds to said resin;

ivb) separating said bound α-amylase from unbound material present in said first partially purified preparation; and ivc) eluting said α-amylase from said resin, whereby a second partially purified α-amylase preparation is obtained.

7. The method according to claim 6 wherein said steps designated (iva)–(ivc) are prepared prior to step (v).

* * * * *